(12) United States Patent
Ghinea et al.

(10) Patent No.: US 8,784,776 B2
(45) Date of Patent: Jul. 22, 2014

(54) USE OF FSH RECEPTOR LIGANDS FOR DIAGNOSIS AND THERAPY OF CANCER

(75) Inventors: Nicolae Ghinea, Creteil (FR); Aurelian Radu, New York, NY (US)

(73) Assignees: Inserm (Institut National de la Sante et de la Recherche Medicale), Paris Cedex (FR); Mount Sinai School of Medicine, New York, NY (US)

( * ) Notice: Subject to any disclaimer, the term of this patent is extended or adjusted under 35 U.S.C. 154(b) by 621 days.

(21) Appl. No.: 12/866,519

(22) PCT Filed: Feb. 18, 2009

(86) PCT No.: PCT/EP2009/051931
§ 371 (c)(1),
(2), (4) Date: Aug. 6, 2010

(87) PCT Pub. No.: WO2009/103741
PCT Pub. Date: Aug. 27, 2009

(65) Prior Publication Data
US 2010/0316572 A1    Dec. 16, 2010

(30) Foreign Application Priority Data
Feb. 18, 2008    (EP) .................................... 08305026

(51) Int. Cl.
*A61K 39/395*    (2006.01)
*A61K 49/00*    (2006.01)

(52) U.S. Cl.
USPC ......... 424/9.1; 424/1.49; 424/9.4; 424/174.1; 424/489

(58) Field of Classification Search
USPC ......... 424/1.49, 9.4, 85.2, 85.7, 130.1, 133.1, 424/134.1, 450, 489; 435/7.23, 70.21, 435/172.2, 240.27, 344; 514/227.8, 236.8, 514/226
See application file for complete search history.

(56) References Cited

U.S. PATENT DOCUMENTS 5,763,202 A * 6/1998 Horoszewicz ............... 435/7.23
2008/0004263 A1* 1/2008 Santora et al. ............. 514/227.8
2009/0041833 A1* 2/2009 Bettinger et al. ............. 424/450

FOREIGN PATENT DOCUMENTS

| EP | 0 359 347 | 8/1989 |
|---|---|---|
| WO | WO 93/19668 | 10/1993 |
| WO | WO 95/15118 | 6/1995 |
| WO | WO 02/09705 | 2/2002 |
| WO | WO 2007/011434 | 1/2007 |
| WO | WO 2007/021621 | 2/2007 |

OTHER PUBLICATIONS

Ben-Josef Edgar et al., Hormone-Refractory Prostate Cancer Cells Express Functional Follicle-Stimulating Hormone Receptor (FSHR), The Journal of Urology, 161, 9790976, 1999.*
Arthur T. Porter et. al., Humoral mechanisms in prostate cancer: A role for FSH, Urologic Oncology, 6, 131-138, 2001.*
Radu, A. et al. "Expression of Follicle-Stimulating Hormone Receptor in Tumor Blood Vessels" *The New England Journal of Medicine*, Oct. 21, 2010, pp. 1621-1630, vol. 363, No. 17.
Mariani, S. et al. "Expression and Cellular Localization of Follicle-Stimulating Hormone Receptor in Normal Human Prostate, Benign Prostatic Hyperplasia and Prostate Cancer" *The Journal of Urology*, Jun. 2006, pp. 2072-2077, vol. 175.
Ben-Josef, E. et al. "Hormone-Refractory Prostate Cancer Cells Express Functional Follicle-Stimulating Hormone Receptor (FSHR)" *The Journal of Urology*, Mar. 1999, pp. 970-976, vol. 161.
Choi, J. et al. "Overexpression of Follicle-Stimulating Hormone Receptor Activates Oncogenic Pathways in Preneoplastic Ovarian Surface Epithelial Cells" *The Journal of Clinical Endocrinology & Metabolism*, 2004, pp. 5508-5516, vol. 89, No. 11, XP-002484160.
Li, Y. et al. "FSH stimulates ovarian cancer cell growth by action on growth factor variant receptor" *Molecular and Cellular Endocrinology*, 2007, pp. 26-37, vol. 267.
Written Opinion in International Application No. PCT/EP2009/051931, Sep. 4, 2009, pp. 1-13.

* cited by examiner

*Primary Examiner* — Michael G Hartley
*Assistant Examiner* — Jagadishwar Samala
(74) *Attorney, Agent, or Firm* — Saliwanchik, Lloyd & Eisenschenk

(57) ABSTRACT

The present invention relates to diagnostic imaging and in particular to the diagnostic imaging and therapy of cancer by means of compositions which specifically target the FSH Receptor expressed by tumor endothelial cells and circulating blood cells.

Figure 1:
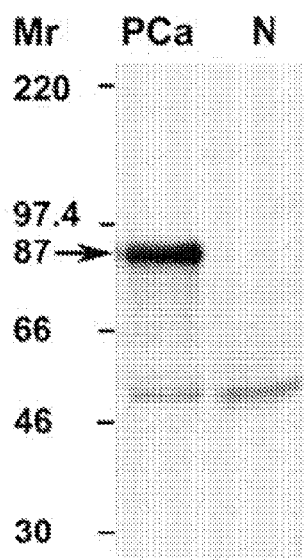

13 Claims, 6 Drawing Sheets

USE OF FSH RECEPTOR LIGANDS FOR DIAGNOSIS AND THERAPY OF CANCER

CROSS-REFERENCE TO RELATED APPLICATION

This application is the U.S. national stage application of International Patent Application No. PCT/EP2009/051931, filed Feb. 18, 2009, the disclosure of which is hereby incorporated by reference in its entirety, including all figures, tables and amino acid or nucleic acid sequences.

FIELD OF THE INVENTION

The present invention relates to diagnostic imaging and therapy and in particular to the diagnostic imaging and therapy of numerous types of cancer, by means of compositions which specifically target FSH Receptor expressed by blood endothelial cells and circulating blood cells.

BACKGROUND OF THE INVENTION

Cancer Diagnostics

Microscopic evaluation of a tissue section taken from a tumor remains the golden standard for determining a diagnosis of cancer. Analysis of genomic DNA, transcribed genes and expressed proteins all add important information to the histological features detected in the microscope images. Tomorrow's diagnosis, prognostic information and choice of treatment will in all likelihood be based on a synoptic evaluation of morphology in conjunction with analyses of nucleic acids and proteins.

Despite remarkable progress within molecular biology, cancer diagnostics still relies on the use of light microscopy. The development of molecular tools has played an important, although as of yet incremental, role to discriminate a cancer cell from a normal cell. The most commonly used method in addition to histochemical staining of tissue sections is immunohistochemistry which allows the detection of protein expression patterns in tissues and cells using specific antibodies. The use of immunohistochemistry in clinical diagnostics has provided a possibility to not only analyze tissue architecture and cellular morphology, but also to detect immunoreactivity in different cell populations. This has been important to support accurate grading and classification of different primary tumors as well as in the diagnostics of metastases of unknown origin. The most commonly used antibodies in clinical practice today include antibodies against cell type markers, e.g. PSA, MelanA, Thyroglobulin and antibodies recognizing intermediate filaments, CD-antigens etc. and markers of malignant potential, e.g. Ki67, p53, HER-2. All tumor markers, measurable either in serum or from tissue specimens, are generally useful in screening, diagnosis, prognosis or monitoring therapy and/or for early indication of relapse. An ideal tumor marker should have high sensitivity, specificity, and reproducibility, and should be included in a practical, easy, cost-efficient test. Such a marker also should have to predict the prognosis and be useful in patient management. Markers that fulfill all these conditions remain to be discovered.

Prostate Cancer

Prostate cancer (PCa) is the most common cancer in males in developed countries [Stenman et al., 2005; Wilson, 2005]. PCa is the second cause of cancer mortality of men in France (11% of deaths by cancer) [www.doctissimo.fr/html/dossiers/cancer_prostate.htm], it affects 17% of the male population in the United States [Wilson, 2005; Jemal et al., 2008], and surpasses lung as the most frequent cancer site in Italy [AIRT working group, 2006]. The incidence of prostate cancer and the rate of death due to the disease increase exponentially with age [Scardino, 2003]. Due to the increase in the percentage of the old population it is expected that in the United States the number of cases of prostate cancer will increase from 234,000 in 2006 to 380,000 in 2025 [Scardino, 2003].

Early detection is essential for curative prostate cancer therapy and for achieving a decrease in prostate cancer mortality. Unfortunately, the available tests can detect only those cancers large enough to be palpable, visible on ultrasound, or capable of elevating the serum level of prostate-specific antigen (PSA).

Screening is performed with digital rectal examination (DRE) and measurement of serum PSA (prostate specific antigen) level. The latter is the most important biochemical marker for the detection of prostate cancer [Ablin et al., 1970 a, b]. However, the utility of PSA tests is limited by their inability to differentiate cancer from clinically irrelevant, non-malignant conditions (benign prostatic hyperplasia, prostatitis, trauma, and urinary retention) [Stenman et al., 2005; Zhu et al., 2006]. Furthermore, it has been shown that the correlation between PSA and cancer is weaker than initially thought, and PSA is regarded now only as a significant marker for prostate size [Stamey et al., 2004]. Patients who have abnormal DRE findings and/or elevated PSA levels have to be further evaluated with prostate needle biopsy, often guided by transrectal ultrasonography [for review, Akin and Hricak, 2007].

Diagnosis and aggressiveness of the tumor is routinely established by using the Gleason system, which is based exclusively on the architectural pattern of glands of the prostate tumor. This histological method evaluates how effectively the cells of any particular tumor are able to structure themselves into glands resembling of normal, very well differentiated gland architecture. In the Gleason grading system the prostate tumor tissues are classified from grade 1 (very well differentiated) to grade 5 (undifferentiated). The sum of the grades of the two most extended tumor areas gives the Gleason score for each patient, which varies from 2 to 10. Since only a small amount of prostate tissue is obtained by needle biopsy, sampling errors are common. High numbers of biopsy samples from different regions of the prostate are necessary to improve cancer detection and risk assessment [Macchia, 2004; Remzi et al., 2005]. In recent years high throughput techniques such as mass spectrometry and microarray analysis led to the discovery of several transcripts and proteins that are overexpressed in prostate tumors [for review, Bradford et al., 2006]. However, none of them is satisfactory for diagnostic purposes [Bradford et al., 2006].

One of the proteins reported to be expressed in prostate tumors but not in normal prostate is follicle stimulating hormone receptor (FSHR). A polyclonal anti-FSHR antibody, revealed focal expression of FSHR in the basolateral areas of secretory epithelia in human hyperplastic prostate tissue, and focal expression but without cell polarity in adenocarcinomas [Mariani et al., 2006]. In contrast to the data of the present invention, Mariani et al. do not mention any FSHR signal in blood vessels.

Another immunohistochemistry study using a different polyclonal antibody reported strong FSHR staining in cancerous prostate glandular structures, and lower levels of staining in the interstitial cells, but no staining in blood vessels. No staining for FSHR was detected in normal prostate glands [Ben-Josef, 1999]. Moreover, the data are questionable, because the molecular weight of the band detected by their antibodies does not correspond to the known size of FSHR, and could be therefore an unrelated protein which crossreacts with their antibody.

Finally a review [Porter et al 1991] suggests that FSH may affect the pathogenesis and progression of prostate cancer and that altering FSH production may prove to be an active therapeutic approach. However, the authors fail to recognize that targeting FSHR expressed on the epithelial tissue prostate tumor is difficult, because FSHR ligands delivered to the blood cannot cross easily by themselves the endothelial barrier [Vu Hai et al., 2004]. No therapeutic or diagnostic method for targeting prostate tumors is so far available for clinical use. A peptide that binds to prostate tumor microvessels in a strain of transgenic mice has been described in 2002 [Arap et al., 2002]. However, it is not known so far if the peptide is suitable for human diagnostic or therapy.

Radiolabeled antibodies anti-prostate specific membrane antigen (PSMA) have been proposed for diagnostic and therapy of prostate cancer. However, only 16% of patients with prostate adenocarcinoma have positive PSMA immunostaining associated with tumor neovasculature [Chang et al., 1999]. In conclusion there are no validated alternative procedures for specific targeting of prostate tumor vasculature.

SUMMARY OF THE INVENTION

The present invention is based on the identification of the presence of FSHR in endothelial cells in tumors or in circulating cells of tumor patients, which has never been mentioned in the prior art.

More particularly, the inventors present evidence that FSHR, which is absent in normal prostate tissue, is highly expressed by endothelial cells of blood vessels, more particularly in microvessels, associated with prostate tumors. This is the first prostate tumor marker that is exposed on the surface of the tumor blood vessel walls, and as a consequence offers unique opportunities for imaging and therapy of prostate cancer. The inventors further present evidence that FSHR is equally expressed by endothelial cells of vessels, more particularly microvessels, associated with kidney, ovary, pancreas, colon, urinary bladder, lung, breast, testis, stomach, brain and liver tumors.

A subject of the invention is thus a FSH receptor (FSHR) ligand for use as an imaging agent, more particularly for use in in vivo diagnostic or imaging of a condition associated with a tumor.

In a particular embodiment, the FSH receptor (FSHR) ligand may be a detectably labeled anti-FSHR antibody or detectably labeled FSH.

Said condition associated with a tumor is preferably selected from the group consisting of prostate cancer, pancreas, colon, kidney cancer, ovary cancer, lung, liver, breast, testis, stomach, brain and urinary bladder cancer.

In a particular embodiment the prostate cancer is prostate adenocarcinoma.

More particularly, the present invention provides a FSH receptor (FHSR) ligand, for use as an imaging agent in in vivo diagnostic or imaging of a tumor, by detecting expression of endothelial FSHR in vessels associated with said tumor.

The FSH receptor (FSHR) ligand is advantageously useful for in vivo localizing or determining the size of a tumor, or for evaluating the severity of a cancer or monitoring the efficacy of an anti-tumor therapy.

Another subject of the invention is a FSH receptor (FSHR) blocking agent, preferably an anti-FSHR antibody, for the treatment of a condition associated with a tumor.

Still another subject is a pharmaceutical composition comprising a FSH receptor (FSHR) ligand which is coupled to an anti-tumor agent.

The FSHR ligands target tumors in a mammal, and can be detected following its administration in vivo, e.g. by SPECT or PET.

The invention further relates to a method for the treatment of cancer, by intravenous delivery of (i) a FSH receptor (FSHR) blocking agent or (ii) a FSH receptor (FSHR) ligand which is coupled to an anti-tumor agent.

In the latter, the anti-tumor agent targets the tumor by the FSHR ligand to which it is coupled.

It is also provided a method for treating cancer, by oral or intravenous delivery of a small molecule compound that modifies FSHR signaling in endothelial cells or in the blood circulating cells that express FSHR.

Administration of FSHR ligand or blocking agent as an imaging agent or as a pharmaceutical composition in therapy may be advantageously performed by intravenous administration.

A further subject of the invention is an in vitro method for diagnosis or prognosis or therapy monitoring of a cancer, which method comprises detecting FSHR in a blood sample of a test subject, wherein the presence in blood of FSHR, more particularly the presence in circulating blood cells of FSHR, is indicative of a cancer.

These and other aspects of the invention are described in more detail herein.

DETAILED DESCRIPTION OF THE INVENTION

Definitions

As used herein, the term "FSHR" denotes the receptor to which the methods of the invention apply. The follicle stimulating hormone receptor or FSH-receptor (FSHR) is a transmembrane receptor that interacts with the follicle stimulating hormone (FSH) and represents a G protein-coupled receptor (GPCR).

As used herein, the term <<FSHR>> denotes also the antigen recognized by the anti FSHR antibody 323 (ATCC as CRL-2689™) and in particular the products of the FSHR gene.

The follicle stimulating hormone, a central hormone of mammalian reproduction, is produced mainly in the anterior pituitary gland and the classical target organs are the ovary and testis. In females, FSH stimulates follicular maturation and oestrogen production through aromatization of androgens [reviewed in Macklon and Fauser, 1998]. In males, FSH functions such as stimulation of Sertoli cell proliferation in immature testis and maintenance of qualitatively and quantitatively normal spermatogenesis have been proposed [reviewed in Plant and Marshall, 2001].

FSH exerts its biological role by binding to the plasma membrane FSH receptor (FSHR).

A cDNA encoding the human FSH receptor (FSHR) has been isolated and sequenced by Minegish et al., 1990. The deduced amino acid sequence of 678 residues contains 7 putative transmembrane segments and displays sequence similarity to G protein-coupled receptors. The 359-residue extracellular domain contains 4 N-linked glycosylation sites. While the protein is approximately 90% identical overall with the rat and mouse FSH receptors, the most highly conserved regions are the putative transmembrane segments, which show 95% similarity.

The FSH receptor is known to be expressed by testicular Sertoli cells and ovarian granulosa cells (Sprengel R 1990, Simoni M. et al 1997).

A exemplary of the amino-acid sequence of the FSHR is available in the SWISSPROT database under the accession number: P23945.

The FSHR affinity-purified by inventors from prostate tissue has a molecular weight of 87 kDa, in agreement with previous studies in ovaries that used the same or other antibodies [Vannier et al., 1996; Ji et al., 2004]. The receptor is glycosylated, and after deglycosylation the molecular weight becomes 76 kDa, close to the computed molecular weight of 76.5 kDa [Vannier et al., 1996].

Since the FSHR was found to be expressed by endothelial cells of vessels associated with tumors, the receptor is also designated Vascular endothelial FSHR or VE-FSHR.

A "tumor" refers to an abnormal growth of tissue resulting from an abnormal multiplication of cells. A tumor may be benign, premalignant, or malignant (i.e., cancerous). A tumor may be a primary tumor, or a metastatic lesion.

The terms "cancer" and "cancerous" refer to or describe the physiological condition in mammals that is typically characterized by unregulated cell growth. Examples of cancers that are associated with tumor formation include brain cancer, head & neck cancer, esophageal cancer, tracheal cancer, lung cancer, liver cancer, stomach cancer, colon cancer, pancreatic cancer, breast cancer, cervical cancer, uterine cancer, bladder cancer, prostate cancer, testicular cancer, skin cancer, rectal cancer, and lymphomas. One of ordinary skill in the art would be familiar with the many disease entities that can be associated with tumor formation.

In certain particular embodiments, the tumor is a cancer, such as prostate cancer, kidney cancer, ovary cancer, pancreas cancer, urinary bladder cancer, lung cancer, colon cancer, breast cancer, testis cancer, brain cancer and liver cancer. In a particular embodiment, the tumor is a prostate cancer.

The term "FSHR ligand" refers to any compound liable to specifically bind to FSHR as defined above. A ligand can thus comprise or can consist of one or several binding moieties. In particular, when a ligand comprises one or several binding moieties, it can also comprises at least one "detectable marker", that is a moiety the presence of which can be readily detected according to methods well known to the man skilled in the art.

Preferably, in the ligands according to the invention, at least one binding moiety is specific for VE-FSHR.

Also preferably, the at least one binding moiety is selected from the group consisting of FSH, an antibody, an antigen-specific antibody fragment, a single-chain variable antibody fragment (scFv), and an aptamer. Methods for producing an antibody, an antigen-specific antibody fragment, a scFv, or an aptamer are well-known to the man skilled in the art.

In a particular embodiment, the FSH receptor (FSHR) ligand is a detectably labeled FSHR-binding chemical agent. In another particular embodiment, it is a detectably labeled FSHR-binding peptide.

The term "FSHR blocking agent" refers to any compound which inhibits or suppresses the expression or activity of the receptor. It is preferably an anti-FSHR antibody. In another particular embodiment, it can be a siRNA, or an antisense molecule. It may also be a chemical agent or a peptide.

More preferably the FSHR ligand or blocking agent is a monoclonal antibody against FSHR. Monoclonal antibodies for FSHR are described, for example, in Vannier et al., 1996. Examples of available monoclonal antibodies for FSHR include the antibody referenced at the American Type Culture Collection (ATCC) as CRL-2689™.

Monoclonal antibodies of the invention or a fragment thereof can be prepared and isolated using any technique that provides for the production of antibody molecules by permanent cell lines in culture. Techniques for production and isolation include but are not limited to the hybridoma technique originally described by Kohler and Milstein (1975); the human B-cell hybridoma technique (Cote et al., 1983).

As intended herein an "antigen-specific antibody fragment" relates to an antibody fragment which retains its specific binding properties towards VE-FSHR according to the invention. Such fragments notably encompass Fab fragments (which can be produced by papain cleavage of antibodies), F(ab')2 fragments (which can be produced by pepsin cleavage of antibodies) or Fab' fragments (which can be produced by pepsin cleavage of antibodies followed by a reducing treatment).

A "scFv" relates to a single-chain variable fragment of an antibody, that is an immunoglobulin short chain variable region and an immunoglobulin large chain variable region linked together by a peptide.

As intended herein an "aptamer" relates to a nucleic acid or peptide molecule, in particular a ribonucleic acid molecule. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. 1997. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena 1999. Peptide aptamers consist of conformationally constrained peptides derived from random peptide libraries or libraries of antibody variable regions displayed by a platform protein, such as *E. coli* Thioredoxin A, that are selected from combinatorial libraries by two hybrid methods (Colas et al., 1996).

In another embodiment, the FSHR ligand may be the Follicle Stimulating Hormone (FSH) like human FSH or recombinant FSH, the more preferably is recombinant human FSH, produced in CHO cells or in bacteria. Bacterially expressed FSH is not glycosylated but may maintain the ability to bind to FSHR, and therefore could induce fewer side effects in its physiological target organs, the testicles and the ovaries.

Examples of commercially available human FSH include those obtained from Serono (Fertinex®, Metrodin HP®). Examples of commercially available recombinant FSH include those obtained from Organon (Follistim®, Puregon®) or from Serono (Gonal-F®).

Derivatives of FSH are further encompassed, e.g. deglycosylated FSH or a peptide fragment derived from the FSH sequence.

The "diagnosis" means the identification of the disease or the assessment of the severity of the disease.

The term "prognosis" means the assessment of the outcome of the condition, i.e. to determine the evolution of the condition, and the risk of worsening.

According to the invention, the term "patient", is intended for a human or non-human mammal affected or likely to be affected with a condition associated with a tumor. Said patient is preferably a human being.

Imaging Methods

Location of FSHR on endothelial cells, as shown by the inventors, allows imaging modes that could not be achieved if FHSR was expressed in tumor cells only.

Prostate tumor imaging attempts have been done using radiolabeled bombesin [Maecke et al., 2005], but FSHR-based imaging is more promising due to much more restricted tissue distribution of FSHR. FSHR-based imaging can guide the collection of biopsies, reducing the large number of samples which are currently collected in order to achieve a robust sampling [Macchia, 2004; Remzi et al., 2005].

The invention thus provides an imaging agent that is designed to target a tumor in a mammal, and which can be detected following its administration to the mammalian body in vivo by imaging procedures e.g. PET. The imaging agent consists of a FSHR ligand, which may be detectably labeled with a detectable molecule or substance, such as a fluorescent molecule, a radioactive molecule or any others labels known in the art to provide (either directly or indirectly) a signal.

As used herein, the term "labeled", with regard to the FSHR ligand, such as an antibody or FSH, is intended to encompass direct labeling by coupling (i.e., physically linking) a detectable substance, such as a radioactive agent or a fluorophore (e.g. fluorescein isothiocyanate (FITC) or phycoerythrin (PE) or Indocyanine (Cy5)) to the ligand, as well as indirect labeling by reactivity with a detectable substance. A FSHR ligand may be labeled with a radioactive molecule by any method known in the art. For example radioactive molecules include but are not limited to radioactive atoms for scintigraphic studies such as $^{123}I$, $^{124}I$, $^{111}In$, $^{186}Re$, $^{188}Re$.

The present invention thus provides an imaging agent of the invention for use in an in vivo diagnostic or imaging method, e.g. Single Photon Emission Computed Tomography (SPECT) or Positron Emission Tomography (PET).

In a further embodiment, a FSHR ligand can be labeled with a gas-filled microvesicle, for use e.g. in contrast enhanced ultrasound imaging. For instance, the FSHR ligand can be associated to or incorporated in a stabilizing envelope of said gas-filled microvesicles according to conventional methods, for instance by covalently binding the ligand to an amphiphilic component, such as a phospholipid. Compositions of gas-filled microvesicles and methods of preparations thereof, suitable for preparing microvesicles bearing a FSHR ligand of the invention, are disclosed, for instance, in WO 91/15244, U.S. Pat. No. 5,597,549, WO 2004/069284, US 2007/0128117, WO 97/29782, U.S. Pat. Nos. 5,605,673, 5,711,933 and 6,333,021, all herein incorporated by reference.

Preferably the method of the invention relates to the in vivo diagnostic or imaging of a condition associated with tumor.

In certain particular embodiments, the tumor is a cancer, such as prostate cancer, kidney cancer, ovary cancer, pancreas cancer, urinary bladder cancer, lung cancer, colon cancer, breast cancer, testis cancer, brain cancer and liver cancer. In a most preferred embodiment the prostate cancer is prostate adenocarcinoma.

As demonstrated in the following examples for prostate cancer, FSHR is highly expressed in blood vessels in tumors, more particularly malignant tumors, but not in normal prostate tissue. The imaging method of the invention makes it thus possible to distinguish between tumors and benign hyperplasias.

Furthermore the FSHR expression may be analysed in conjunction with the Gleason score. The Gleason score is based on the architectural pattern of the glands of the prostate tumor. It evaluates how effectively the cells of any particular cancer are able to structure themselves into glands resembling those of the normal prostate. The ability of a tumor to mimic normal gland architecture is called its differentiation, and experience has shown that a tumor whose structure is nearly normal (well differentiated) will probably have a biological behaviour relatively close to normal—that is not very aggressively malignant. Gleason grades and stages have been assigned according the World Health organization guidelines 2004.

A particular subject of the invention is a method for collecting imaging data, which method comprises the steps consisting of:
 a) providing an imaging agent comprising a detectably labeled FSH receptor ligand;
 b) administering a patient with said imaging agent;
 c) collecting imaging data in said patient.

Another subject of the invention is a method for diagnosing a condition associated with a tumor, which method comprises the steps consisting of:
 a) providing an imaging agent comprising a detectably labeled FSH receptor ligand;
 b) administering a patient with said imaging agent;
 c) collecting imaging data in said patient;
 d) detecting the tumor and diagnosing the condition associated with the tumor.

In a preferred embodiment, the imaging agent of step a) is radioactively labeled FSH or radioactively labeled antibodies against FSHR.

The present invention further provides a method for monitoring the efficacy of an antitumor agent (unrelated to FSH or FSHR) by sequential imaging of the tumor size using a FSHR ligand.

Examples of the tumor therapies include but are not limited to chemotherapy, cryotherapy and radiotherapy.

In a preferred embodiment, the tumor therapy is a hormonal therapy.

This aspect of the invention relates to methods of determining the efficacy of agents for treating a cancer, such as prostate adenocarcinoma, in a subject who has been treated with an agent, by detecting the expression of endothelial FSHR in blood vessels, in particular in microvessels, associated with tumors. The expression of FSHR can be detected by any of the methods described above using the imaging agent of the invention.

The level of FSHR expression which is utilized as a diagnostic marker for drug efficacy can be determined by using the imaging agent in the same subject prior to and after drug treatment. A significant difference is significant of the drug achieving its effect. For example successful hormonal treatment of prostate tumors is expected to be accompanied by loss or strong diminution of FSHR expression, which can be detected using the imaging method of the invention.

In vitro diagnostics

The inventors have also discovered that cells expressing FSHR accumulate in circulating blood cells of patient with a tumor status. Accordingly, blood level of FSHR can be used as a marker of a cancer.

In certain particular embodiments, the tumor is a cancer, such as prostate cancer, kidney cancer, ovary cancer, pancreas cancer, stomach cancer, urinary bladder cancer, lung cancer, colon cancer, breast cancer, testis cancer, brain cancer and liver cancer. In a particular embodiment, the tumor is a prostate cancer. In a most preferred embodiment the prostate cancer is prostate adenocarcinoma.

On this basis, the invention provides an in vitro method for diagnosis or prognosis of a cancer, which method comprises detecting FSHR in a blood sample of a test subject, wherein the presence in blood of FSHR, is indicative of a cancer.

The blood sample may consist in whole blood.

Peripheral blood is preferred, and polymorphonuclear cells (PMNs) are the preferred cells from which FSHR can be detected and/or quantified. In a preferred embodiment, the method for diagnosis or prognosis of a tumor disease comprises a preliminary step of extracting peripheral blood PMNs.

The presence of FSHR in blood, is indicative of a tumor disease. As detailed in the example and in FIGS. 10 and 11, FSHR-positive cells with polymorphonuclear aspect are visible in the lumen of blood vessels from tumors, but not in the vessels of benign hyperplasia.

When the test subject is a patient already diagnosed with a tumor disease, the quantity FSHR of said patient, compared to a former value in the same patient, is indicative of the level of activity of the tumor disease. It can be useful to determine the efficacy of a therapy, by monitoring the progression of the disease in the patient subjected to a defined therapy. The method of the invention is also particularly useful to assess the status of a patient diagnosed with cancer.

In vitro detection of FSHR in circulating cells can be easily achieved by any standard technique, e.g. ELISA or flow cytometry.

In a typical ELISA assay, the blood sample to test is contacted with anti-FSHR antibody, preferably immobilized in a solid format. Unbound cells are removed by washing, and the remaining cells are incubated with a labeled (e.g. biotinylated) anti-FSHR antibody. Detection of FSHR in the blood sample is then revealed and quantified, e.g. after incubation with streptavidin peroxidase, followed by a suitable color-generating reagent.

Therapeutic Application:

Location of FSHR on endothelial cells, as shown by the inventors, allows therapy by attacking the tumor blood vessels.

Another subject of the invention is a FSH receptor (FSHR) blocking agent, preferably an anti-FSHR antibody, for the treatment of a condition associated with a tumor.

The FSHR blocking agent may act by suppressing the activity or expression of the FSHR receptor. According to an aspect, the blocking agent is an inhibitor of the expression of FSHR gene. Inhibitors of the expression of FSHR gene include for instance antisense RNA, RNAi or DNA molecules, or ribozymes. In another embodiment the blocking agent, which is preferably an antibody, can be coupled to a radioisotope, which kills the tumor cells only, by irradiation in the immediate vicinity and spares the healthy tissue, as alternative to seeds or beam radiation (see Parry et al, 2006).

Still another subject is a pharmaceutical composition comprising a FSH receptor (FSHR) ligand which is coupled to an anti-tumor agent. Such a composition is particularly useful for treating a condition associated with a tumor.

The FSHR ligand is then used as a specific tool for direct targeting of tumor for in vivo delivery of antitumor agents.

In certain particular embodiments, the tumor is a cancer, such as prostate cancer, kidney cancer, ovary cancer, pancreas cancer, urinary bladder cancer, lung cancer, colon cancer, breast cancer, testis cancer, brain cancer and liver cancer. In a particular embodiment, the tumor is a prostate cancer. In a most preferred embodiment the prostate cancer is prostate adenocarcinoma.

The antitumor agents may block flow in the tumor vessels or destroy the tumor endothelial cells, or destroy or block the proliferation of tumor cells.

They may be chosen between anticancer drugs, toxins, genes, siRNAs, and small molecules:

Examples of antitumor agents are:

1. antibody targeted radiotherapy: Antibody coupled to radioisotope, which kills by irradiation only the tumor cells in the immediate vicinity and spares the healthy tissue, as alternative to seeds or beam radiation (see Parry et al, 2006);

2. peptides that destroy the targeted cells (see Arap et al 2002; Leuschner and Hansel, 2005);

3. genes coding for proteins that kill preferentially the newly formed blood vessels (see Hood et al 2002);

4) anticancer drugs (i.e. chemotherapeutic agents) that can destroy cancer cells, when coupled to a FSHR ligand. The term "chemotherapy" usually refers to cytotoxic drugs which affect rapidly dividing cells in general. Chemotherapy drugs interfere with cell division in various possible ways, e.g. with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can. Hence, chemotherapy has the potential to harm healthy tissue, especially those tissues that have a high replacement rate (e.g. intestinal lining). These cells usually repair themselves after chemotherapy.

5) small molecules, specific for the deregulated proteins of cancer cells Such small molecules are generally inhibitors of enzymatic domains on mutated, overexpressed, or otherwise critical proteins within the cancer cell. Prominent examples are the tyrosine kinase inhibitors imatinib and gefitinib.

Location of FSHR in circulating blood cells, as shown by the inventors, further allows therapy by targeting such circulating blood cells.

Another subject of the invention is thus a FSH receptor (FSHR) ligand that modulates abundance of FSHR-expressing circulating blood cells, or expression or signalling of FSHR by the circulating blood cells, for use in treating cancer, preferably in a form for intravenous administration.

It is further provided a method for treating cancer, which method involves modulating (i.e. reducing or stimulating) abundance of FSHR-expressing circulating blood cells, or expression or signalling of FSHR by the circulating blood cells.

Administration:

The imaging or pharmaceutical compositions are generally formulated in combination with a biocompatible carrier, in a form suitable for mammalian administration.

In a preferred embodiment, the imaging composition is a radiopharmaceutical composition.

The "biocompatible carrier" is a fluid, especially a liquid, in which the imaging agent is suspended or dissolved, so that the composition is physiologically tolerable, i.e. can be administered to the mammalian body without toxicity or undue discomfort. The biocompatible carrier medium is suitably an injectable carrier liquid such as sterile water for injection; an aqueous solution such as saline; an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like).

In an additional aspect, the present invention provides kits for the preparation of the imaging or pharmaceutical compositions of the invention. The reaction medium for reconstitution of such kits is preferably a "biocompatible carrier" as defined above, and is most preferably aqueous. Suitable kit containers comprise a sealed container which permits maintenance of sterile integrity and/or radioactive safety, plus optionally an inert headspace gas (e.g. nitrogen or argon), whilst permitting addition and withdrawal of solutions by syringe.

The kits may optionally further comprise additional components such as, when needed, a radioprotectant, antimicrobial preservative, pH-adjusting agent or filler.

The term "radioprotectant" refers to a compound which inhibits degradative reactions such as redox processes, by trapping highly-reactive free radicals, such as oxygen-containing free radicals arising from the radiolysis of water. The radioprotectants of the present invention are suitably chosen from: ascorbic acid, para-aminobenzoic acid, gentisic acid (i.e. 2,5-dihydroxybenzoic acid) and salts thereof with a biocompatible cation. The "biocompatible cation" and preferred embodiments thereof are as described above.

The term "antimicrobial preservative" refers to an agent that inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the composition post-reconstitution. Suitable antimicrobial preservative(s) include: the parabens, i.e. methyl, ethyl, propyl or butyl paraben or mixtures thereof, benzyl alcohol, phenol, cresol, cetrimide and thimerosal.

The term "pH-adjusting agent" means a compound or mixture of compounds useful to ensure that the pH of the reconstituted kit is within acceptable limits (approximately pH 4.0 to 10.5) for human or mammalian administration. Suitable such pH-adjusting agents include pharmaceutically acceptable buffers, such as tricine, phosphate or TRIS, and pharmaceutically acceptable bases such as sodium carbonate, sodium bicarbonate or mixtures thereof. When the precursor is employed in acid salt form, the pH adjusting agent may optionally be provided in a separate vial or container, so that the user of the kit can adjust the pH as part of a multi-step procedure.

The term "filler" is meant means a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

The invention will further be illustrated by the following figures and examples.

Figure Legends

FIG. 1. The FSH receptor is expressed in prostate tumors but not in normal prostate. Equal amounts (1 mg of total protein) of Triton X-100 extracts from cancerous (PCa) and normal (N) tissues were immunoprecipitated with the FSHR323 monoclonal antibody, resolved on reducing SDS-PAGE and transferred to nitrocellulose membranes. The samples were probed with FSHR323 antibody. The position of molecular mass markers is shown on the left. A similar situation was found in tissue obtained from four other patients. The faint band corresponds to the mouse IgG used for immunoprecipitation.

Figure 2:
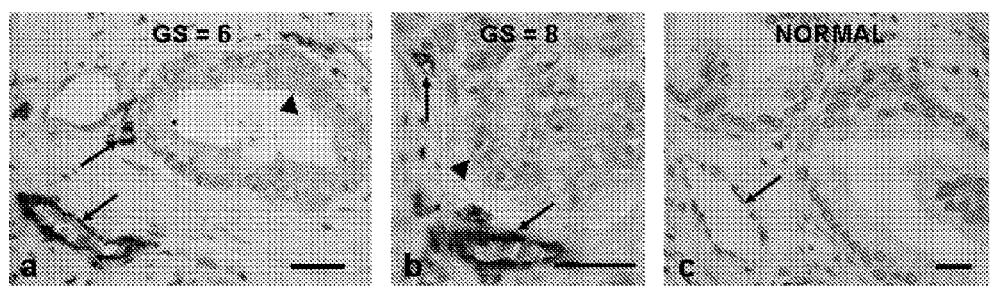

FIG. 2. FSHR expression in prostate cancer versus normal prostate tissue: Immunohistochemistry with FSHR323 monoclonal antibody. (a, b) Prostate cancer tissues from patients with Gleason scores (GS) 6 and 8, respectively. The FSHR staining suggests abundant receptor expression in blood vessels (arrows) associated with the prostate cancer. A faint signal is visible in epithelial cells (arrowheads). (c) Normal prostate tissue processed as in a and b. Note the absence of staining with the anti FSH receptor antibody. Bar, 20 µm.

Figure 3:
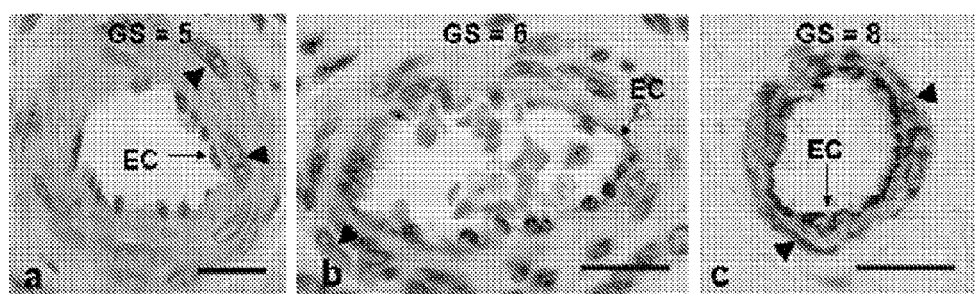

FIG. 3. The arteriolar endothelium expresses FSHR only above Gleason score 6. GS, Gleason score; EC, arteriolar endothelial cell; arrow head, smooth muscle cell. Bar, 20 µm.

Figure 4:
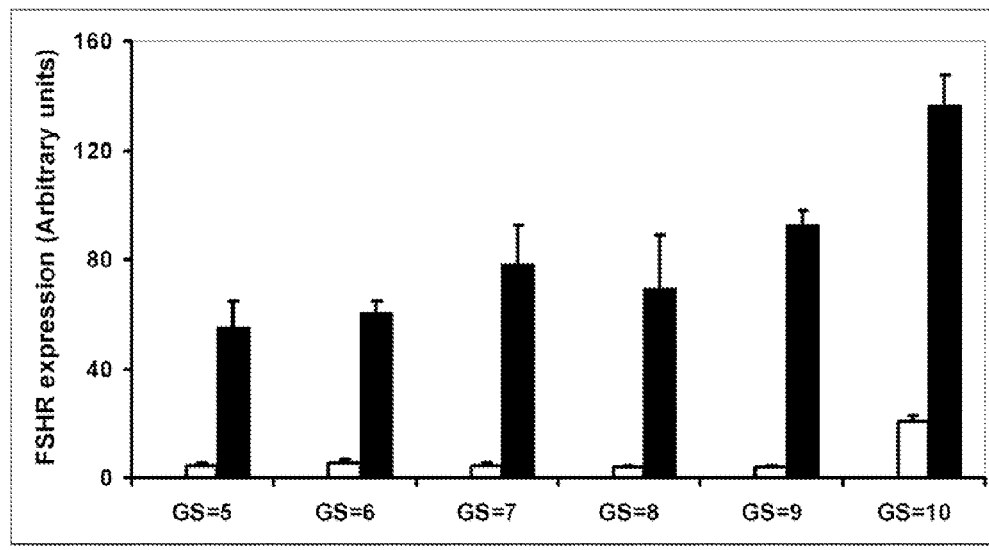

FIG. 4. FSHR expression in prostate. Intensity of FSHR signal over the endothelial cells of blood vessels. Closed bars, average intensity over the endothelial cells of individual blood vessels using digital images similar to those in FIG. 2. Open bars, intensity of FSHR signal measured for areas of tissue excluding the blood vessels.

Figure 5:
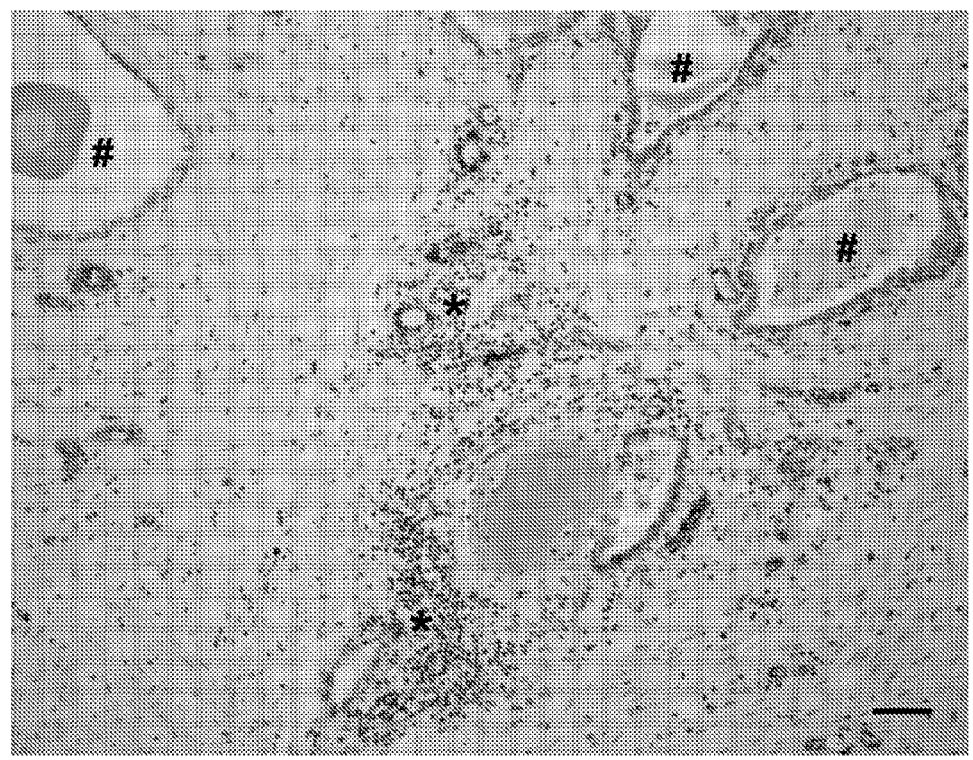

FIG. 5. Blood vessels in proximity of the inflammatory leukocyte infiltrates express strongly FSHR. #, lumen of normal glands; *, centroid of compact inflammatory area. Bar, 50 µm.

Figure 6:
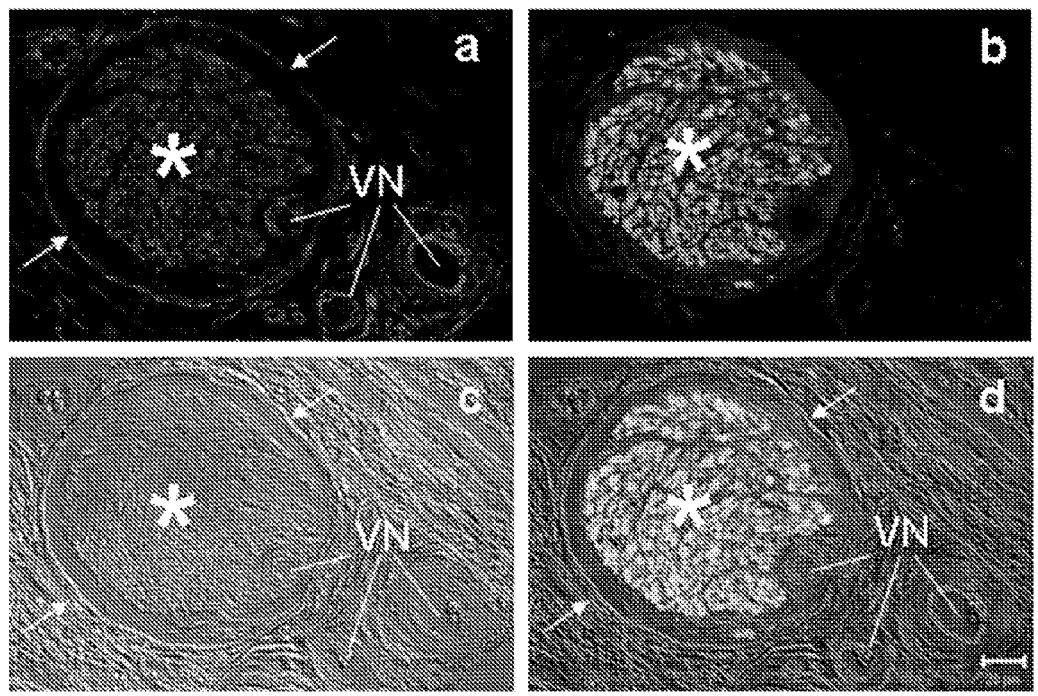

FIG. 6. Prostate nerves and their associated blood vessels in cancer tissues express FSHR. Confocal microscopy images: a, FSHR; b, S-100 protein—a Schwann cell marker; c, differential interference contrast; and d, merge. VN, vasa nervorum; arrows, perineurial sheaths. Bar: 20 µm.

Figure 7:
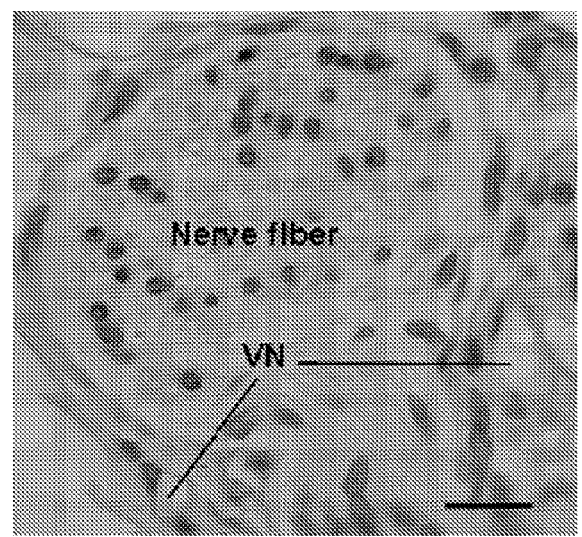

FIG. 7. Prostate nerves and their associated blood vessels in BPH do not express FSHR. VN—vasa nervorum. Bar: 20 µm.

Figure 8A:
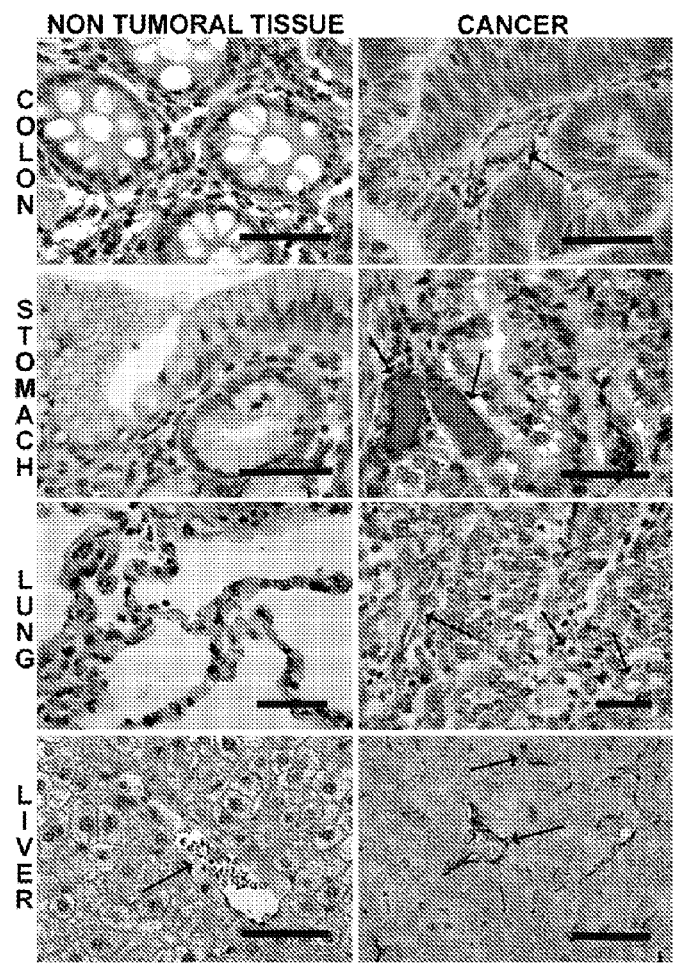
Figure 8B:
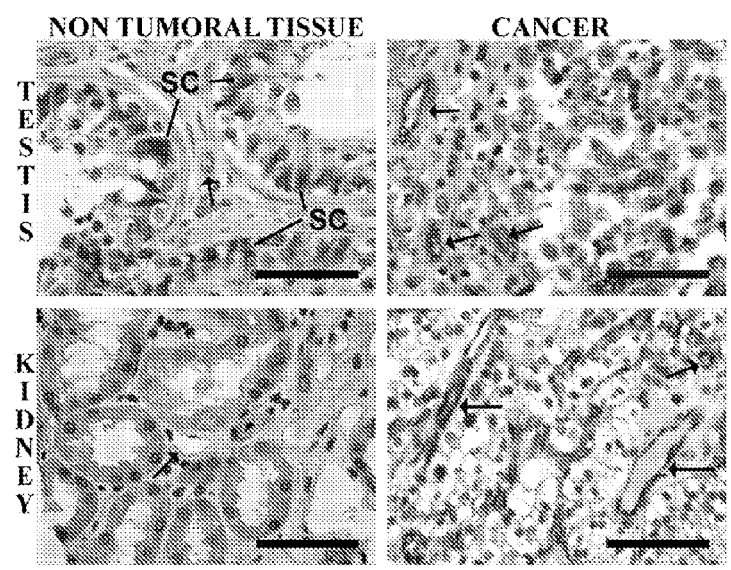
Figure 8C:
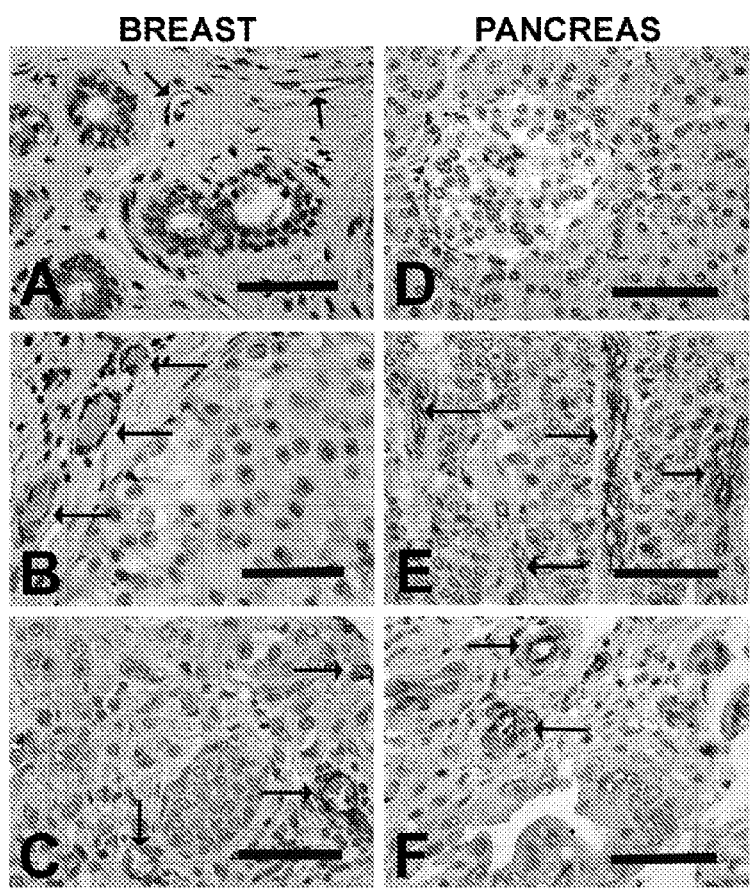

FIG. 8. FSHR is expressed by blood vessels in other tumor types.

A) colon tumor, stomach adenocarcinomas, Non Small Cells Lung (NSCL) adenocarcinomas, and liver adenocarcinomas. B) testis tumor (seminoma) and kidney clear cell tumor. In the normal testis tissue, Sertoli cells (SC), known to express FSHR, are positive. A faint FSHR signal is barely visible in the blood vessel present in the same image (arrow). Blood vessels in the normal testis are known to express FSHR, which is responsible for the transcytosis of FSH across the testicular barrier (Vu Hai et al., 2004). C) Representative images for breast control tissue (a), breast cancer in situ (b) and invasive breast cancer (c). The panels on the right show normal pancreatic tissue (d), a pancreatic endocrine tumor (e) and a pancreatic adenocarcinomas (f). Bar, 50 µm. The controls for all tumor types consisted in normally appearing tissue located further than 10 mm outside the tumors, in the specimens obtained by surgery performed for tumor removal.

Figure 9:
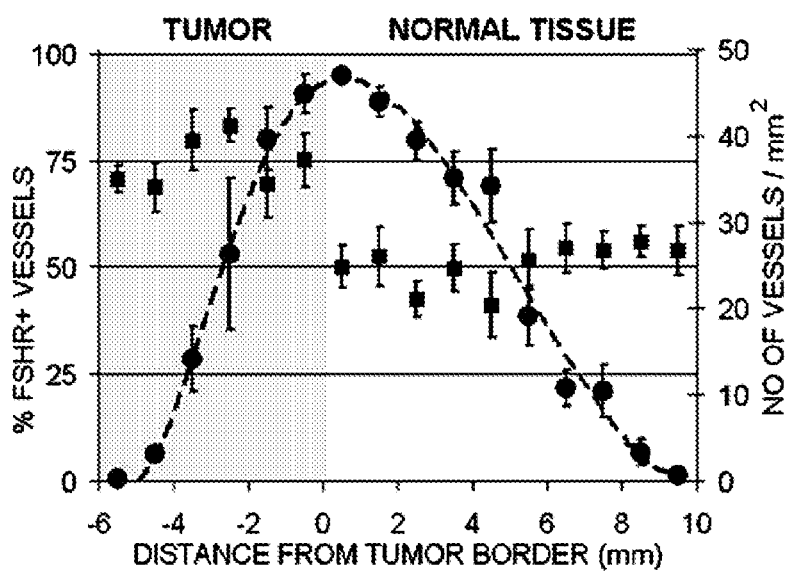

FIG. 9. Distribution of FSHR-stained vessels at the periphery of prostate tumors.

The blood vessels were visualized using anti von Willebrand Factor antibodies followed by Alexa 488 (green) secondary antibodies, while FSHR-stained vessels were visualized by the FSHR323 antibody followed by Alexa 555 (red) labeled secondary antibodies. The vessels were counted on 148 microscopy digital images from tumors of 5 patients. Horizontal axis—the distance from the demarcation line between the tumor and the normally appearing tissue (the shaded area and the negative values represent the interior of the tumor). Left vertical axis—the % of FSHR-expressing vessels. Right vertical axis—the number of vessels/mm$^2$. Squares—the number of vessels per mm$^2$; the discs and the interrupted line represent the % of FSHR-expressing vessels.

Figure 10:
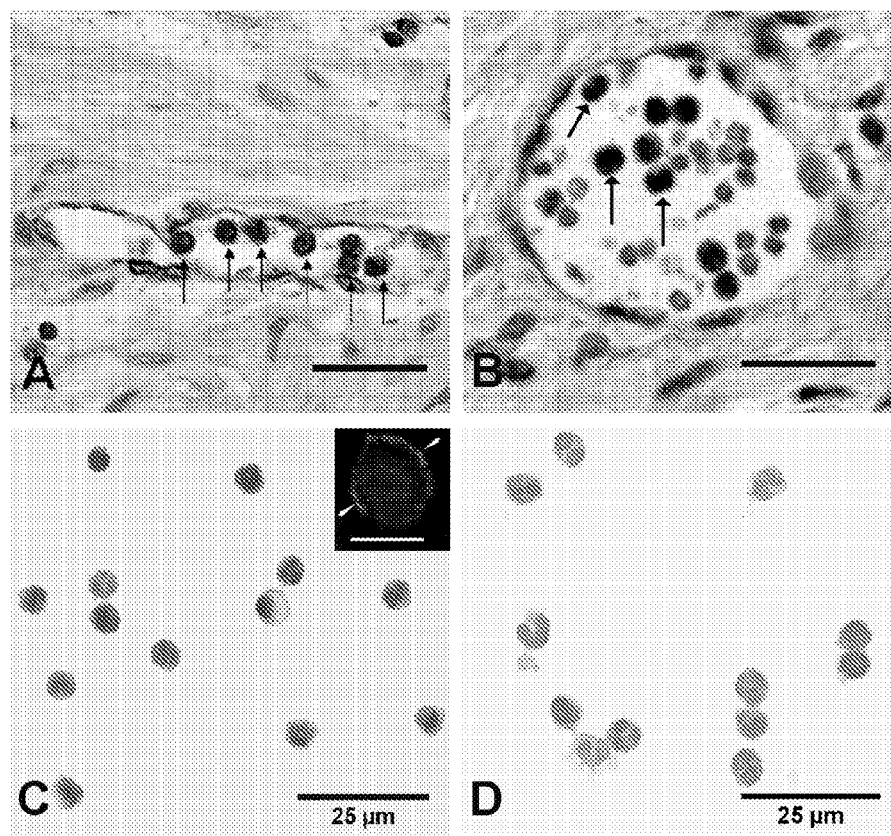

FIG. 10. FSHR is expressed in polymorphonuclear cells of prostate cancer patients. FSHR-positive cells that have the aspect of polymorphonuclear cells (arrows) are visible in the lumen of blood vessels from tumors (A) and also at more than 10 mm distance from the tumor border (B) which suggests that these cells are present in the general circulation and not only in the tumors. C. A preparation enriched in polymorphonuclear cells from prostate cancer patients reveals FSHR staining in polymorphonuclear-like cells but not in other leukocytes. D. A similar preparation from healthy donor does not show any FSHR positive circulating blood cells.

Figure 11:
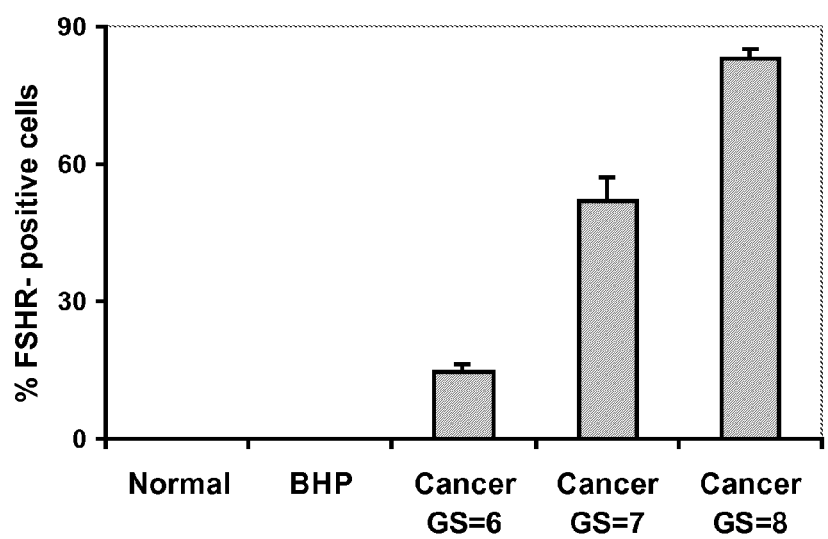

FIG. 11. The percentage of circulating blood cells that express FSHR increases with the severity of the disease. Vertical axis—percentage of FSHR—positive cells among the cell fraction isolated from blood as described in the text. Error bars—standard errors; BPH—Benign Prostate Hyperplasia; GS—Gleason Score.

Material and Methods

Tissue specimens. The donors did not receive any medication. Tumor specimens were fixed in 10% formalin for 48 hours, cut in 5 mm thick tissue sections, washed thoroughly with PBS, dehydrated in graded ethanol and xylene, and embedded in paraffin. Large 5 µm sections of 1.5-2.5 cm were cut from the paraffin blocks. Several unfixed prostate samples were frozen on dry ice and stored in liquid nitrogen until sectioning with a cryostat for immunofluorescence microscopy and/or immunoprecipitation and immunoblotting experiments.

Tumor specimens have been histologically reviewed by five study investigators. For prostate cancer the Gleason grades and stages have been assigned according to the World Health organization guidelines 2004. The other tumor types have been graded histologically based on the AJCC standards. The types of tumors analyzed and number and sex of patients are presented in Table I.

TABLE I

Tumor types

| TUMOR | | No of Patients | |
| --- | --- | --- | --- |
| | HISTOPATHOLOGICAL TYPE | F | M |
| PROSTATE | Adenocarcinomas | | 550 |
| | Benign hyperplasia | | 300 |
| BREAST | In situ carcinomas | 56 | |
| | Invasive carcinomas | 112 | |
| COLON | Carcinomas | 6 | 9 |
| PANCREAS | Carcinomas | 27 | 36 |
| | Endocrine tumors | 22 | 19 |
| URINARY | In situ urothelial carcinomas | 62 | 64 |
| BLADDER | Adenocarcinomas | 41 | 36 |
| KIDNEY | Clear cell renal carcinomas | 25 | 39 |
| LUNG | Adenocarcinomas | 9 | 6 |
| LIVER | Hepatocellular carcinomas | 4 | 11 |
| STOMACH | Adenocarcinomas | 3 | 3 |
| TESTIS | Seminoma | | 5 |
| | Sertoli cell carcinoma | | 1 |
| | Leydig cell tumors | | 2 |
| OVARY | Epithelial carcinomas | 6 | |

A patient with brain tumor was also tested.

Tissue microarrays (TMA) were constructed using archived formalin-fixed paraffin embedded [Kononen et al., 1998]. Briefly, the original slides were reviewed by the study pathologists, and slides containing tumor or normal appearing tissue were selected and marked with coloured ink. For each patient, 3-4 cylindrical cores (0.6 mm in diameter) of tumor and 3-4 cores of normal (non-malignant, non dysplastic) prostate tissue were transferred from the selected areas of the paraffin blocks to the recipient blocks. Each recipient block regrouped tumors for 28 to 40 patients. Large serial 5 µm-thick sections of the TMA blocks, containing all the cores, were cut and stained with haematoxylin-eosin to verify that the cores adequately represented the diagnosed areas. Images covering the full area of each core were obtained from one section of each TMA.

Immunohistochemistry. Standard indirect immunoperoxidase procedure was used for immunohistochemistry. Tissue sections were attached to SuperFrost slides, deparaffinized with toluene, gradually dehydrated in ethanol, and washed with running tap water for 60 min. Access to tissue antigen sites for antibody attachment was enhanced by incubating slides at 90° C. for 40 min with 10 mM citrate buffer, pH 6. After cooling for 20 min at room temperature and after each subsequent step, slides were rinsed with PBS. To block endogenous peroxidase activity the sections were incubated with 6% hydrogen peroxide (15 min at room temperature). Sodium borohydride (50 mg/ml) was used to quench the free aldehyde groups (20 min). Non specific binding of antibodies was blocked by incubating slides with 2% goat serum in PBS (blocking buffer) for 2 hours at room temperature. FSHR was detected by incubating the slides with 5 µg/ml of the anti-FSHR monoclonal antibody 323 [Vannier et al., 1996] in blocking buffer (overnight, 4° C.). Goat antimouse IgG (Fc specific) coupled to horseradish peroxidase (Sigma, 1:200 dilution) was used as secondary antibody. As chromogen we used 3-amino-9-ethyl-carbazole (AEC; Sigma). The chromogenic development was monitored for 15 minutes through a light microscope. The sections were washed in distilled water and counterstained with a weak Mayer's haematoxylin. The slides were mounted in Dako Glycergel mounting medium.

Immunocytochemistry of circulating blood cells. Blood collected on EDTA was treated with ammonium chloride to lyse the red blood cells and polymorphonuclear cells have been enriched by centrifugations at 55 g (Eggleton et al., 1989). The cells have been fixed overnight with 4% formaldehyde at 4° C. and attached to polylysine-coated microscope slides. FSHR was detected with anti-FSHR monoclonal antibody 323 as described above.

Indirect immunofluorescence confocal microscopy. Serial cryostat sections (7 µm) of Tissue-Tek-embedded unfixed frozen prostates were collected on SuperFrost slides and air dried. The sections were fixed with 3% paraformaldehyde in PBS for 15 min at room temperature. The free aldehyde groups were quenched by treating sections with 50 mM NH$_4$Cl in PBS for 15 min. To block the non specific binding of antibodies the slides were incubated 1 hour at room temperature with 2% goat serum in PBS. FSHR was detected by incubating sections sequentially with antiFSHR323 antibody (3 µg/ml) in GS-PBS for 2 hours at room temperature and with goat anti-mouse IgG-Alexa 555 (Molecular Probes; dilution 1:750 in blocking buffer; 1 hour). Double labeling experiments have been done with prostate sections incubated with a mixture of anti FSHR323 antibody (3 µg/ml in blocking buffer) and either the rabbit polyclonal anti-von Willebrand factor, a specific marker of endothelial cells (Sigma; dilution 1:1000) A mixture of goat-anti mouse IgG-Alexa 555 and goat-anti rabbit Ig-Alexa 488 (Molecular Probes; dilution 1:750) has been used as secondary antibodies. In some experiments nuclei were detected by incubating slides for 10 min with TOTO-3 (Molecular Probes; dilution 1:1000 in PBS). The slides were mounted in Dako® fluorescent mounting medium containing 15 mM sodium azide and examined with a Zeiss 510 Confocal Laser Scanning Microscope. Negative controls consisted of prostate samples incubated only with fluorescent secondary antibody mixtures. Immunofluorescence confocal microscopy was also done on paraffin sections using a similar method except that the concentration of the FSHR323 antibody was 5 µg/ml.

Immunoprecipitations followed by SDS-PAGE and western blotting were carried out as previously described [Vannier et al., 1996] by using 200 mg wet prostate tissue as starting material. Immunopurified FSHR from L cells stably expressing the protein receptor was used as control.

Quantitation of the FSHR signal on blood vessels in immunohistochemistry images. Briefly, for each vessel profile we computed the area of the vessel excluding the lumen, as well as the total FSHR signal over this area. The average intensity of the FSHR signal over each vessel was then computed by dividing the total FSHR signal to the area. The above values have been extracted from digital images of each vessel profile using Adobe Photoshop, as described below. The outer contour of the vessel was delineated using the "Lasso" tool, and the selected area was copied and pasted in a new file (referred to here as file A). The stained areas were delineated in this file using in the commands "Select" and "Colour range" [Tolivia et al., 2006] using fuzziness 30. (The brown-red colour specific for the peroxidase reaction product was initially selected from a representative image and stored in a file using the Save command from the "Colour Range" menu. This file was subsequently loaded for analysis of each image.) The selected area was copied in a new file (B). Similar operations were performed for the inner diameter of the vessel, generating the files C and D. (The background of files A-C was black). The "Merge Layers" command was applied to all files, and files B and D were converted to gray scale. In a second stage of the analysis numerical values were extracted from the files A-C using the NIH ImageJ software. The inner and outer areas of each vessel profile have been measured from the files A and C using the "Freehand" tool followed by the "Analyze" and "Measure" commands. Then the whole area of the images B and D was selected using the "Rectangle" tool, and the sum of all pixels have been derived using "Analyze" and "Measure". (The areas outside the vessels have no contribution, because they are black.) The values have been introduced into an Excel file. The values corresponding to the vessel wall have been subsequently obtained by subtracting the values for the lumen from the values for the whole vessel profile. The average intensity of the staining of the vessel wall was computed by dividing the total signal over the vessel wall to the area of the vessel contour.

Results:

1. The FSH Receptor is Expressed in Prostate Tumors

Receptor preparations from prostate tissues, enriched by immunoprecipitation with FSHR323 antibody, were analyzed by immunoblotting using FSHR18 antibody. A band of approximately 87 kDa was detected in prostate cancer tissues (FIG. 1, lane PCa). No FSHR was observed in extracts from normally appearing tissue in prostates from prostate cancer patients (lane N). The size of the detected band is the same as the 87 kDa mature glycosylated form previously detected in human ovarian tissues [Vannier et al., 1996].

2. Immunohistochemical studies indicate that FSHR is abundantly expressed in blood vessels in prostate tumors but not in normal tissue The localization of the FSHR was next investigated by immunohistochemistry using the FSH323 antibody. Large rectangular sections (1.5-2.5 cm) have been used. Most of these sections contained both tumor tissue and normally appearing areas. As generally known, most prostate tumors are localized at the periphery of the prostate and almost none arise in the central zone [De Marzo et al., 2007]. In images obtained from the peripheral tumor areas of patients with Gleason scores of five or higher a faint signal was visible in epithelial cells (arrowhead in FIG. 2a and b). In contrast, the vast majority of epithelial cells in normally appearing areas at the periphery show no FSHR staining (FIG. 2c). [Small focal areas of basolateral FSHR staining associated with secretory cells are infrequently visible in normally appearing peripheral tissue (not illustrated)]. No FSHR signal is detectable in epithelial cells in normally appearing tissue in the central area of the same prostates. The majority of the blood vessels in the tumor tissue are abundantly stained (arrows in FIG. 2, a and b), while most of the blood vessels in the normally appearing peripheral tissue are not stained (arrows in FIG. 2c). The abundant FSHR expression in tumor blood vessels was seen without exception in all 50 patients that have been diagnosed with Gleason scores of five or higher. (No tissues from patients with Gleason score lower than five were available for analysis). No FSHR expression was present in blood vessel profiles of normal tissue in central areas (not illustrated). As an exception, blood vessels are stained in inflammatory areas found in normal areas in both peripheral and central locations (see below). The prostate benign hyperplasias do not express FSHR either in epithelial cells, or in blood vessel walls, with the exception of some inflammatory areas (see below).

3. Endothelial cells are the main sites of FSHR expression in tumor vessels

The size and appearance of the blood vessels profiles stained for FSHR is compatible with the conclusion that they represent capillaries, venules, and arterioles. Some of these vessels are constituted, besides endothelial cells, of pericytes (some capillaries and postcapillary (pericytic) venules) and smooth muscle cells (arterioles and muscular venules) [Simionescu and Simionescu, 1988]. Therefore it is relevant to clarify which of these cells express FSHR in tumors. A marker specific for endothelial cells, von Willebrand factor, indicated that in capillaries and venules the FSHR is expressed by endothelial cells and by no other cell types that constitute the blood vessel walls. In arterioles, besides the endothelium the smooth muscle cells are stained at all Gleason scores analyzed (5 to 10) (FIG. 3). By comparison, the smooth muscle cells in muscular venules are not stained at any Gleason score (not illustrated). While the endothelium of capillaries and venules is stained for FSHR at all analyzed Gleason scores (5 to 10), the arteriolar endothelium is stained only at Gleason scores 6 and higher (FIG. 3 b, c). This pattern of endothelial and smooth muscle cells staining was valid for tissues from all the 50 patients that have been analyzed.

4. Quantitation of FSHR expression in function of the Gleason score.

The average signal intensity over the endothelial cells of individual blood vessels was determined using digital images similar to those in FIG. 2. Only capillaries and postcapillary venules have been measured. Arterioles have not been measured because of the complication introduced by the presence, besides stained endothelial cells, of stained smooth muscle cells. There is a clear tendency for an increased expression of FSHR at high Gleason scores (on average 118±8(SEM) units for scores 9 and 10 vs. 64±7 for Gleason scores 5 and 8, $p<0.0005$) (FIG. 4, closed bars). The intensity of FSHR signal was also measured for areas of tissue excluding the blood vessels (FIG. 4, open bars). In this case too the expression is higher at the highest score (18.4±1.1 units at Gleason score 10 vs. 3.8±0.3 units for Gleason scores 5 to 9, $p<1.7\times10^{-11}$). It should be noted that the FSHR signal is much higher for endothelial cells than for the rest of the tissue (approx 6 to 10 fold higher).

5. Vascular FSHR appears also in non tumoral prostate tissue in vicinity of inflammatory leukocyte infiltrates For each of the fifty patients the large paraffin sections contained at least one compact area of high density of inflammatory cells (FIG. 5), without clear association with the tumor or normal zones. A consistent observation was that the vast majority of the blood vessels in the interior or in proximity of the leukocyte infiltrates expressed strongly FSHR, even if the surrounding tissue had normal, non tumoral aspect. This effect was noticed for blood vessels up to a distance of 3.5 mm (average 2±0.75 (standard deviation), n=34) from the proximal edge of the inflammatory area.

Interestingly, the lumen of most blood vessels associated with inflammatory areas is occupied, besides erythrocytes, by numerous nucleated cells. In contrast, the lumen of most blood vessels which do not have nearby leukocytes is either empty or shows erythrocytes and very few nucleated cells.

In benign prostate hyperplasias, which occur in the transitional zone of the prostate [De Marzo et al., 2007], 5 of the 20 patients analyzed had inflammatory infiltrates. Approximately 20% of the inflammatory areas showed FSHR expression both in blood vessels and faint basolateral staining in secretory epithelial cells.

6. Nerves and their associated vessels express FSHR

The prostate is a richly innervated organ. Two neurovascular bundles run laterally along the rectal surface of the gland, and other nerves run along the inner surface of the capsule before branching out into the prostatic parenchyma [Powell, 2005]. All nerves are accompanied by blood vessels (vasa nervorum), some of which penetrate the epineurial sheaths. We noticed intense FSHR staining of Schwann cells in all nerve fibers in peripheral areas affected by cancer at all Gleason scores. The blood vessels associated with these nerves express also FSHR (FIG. 6). A stronger staining of blood vessels was seen in areas containing both nerves and inflammatory infiltrates.

In normally appearing peripheral tissues of cancer patients the nerves show also intense FSHR staining of Schwann cells and vasa nervorum at all analysed Gleason scores (5-10).

In a patient that had no tumors but was subjected to radical prostatectomy due to PBH, the majority of nerves and their associated vessels in the peripheral areas of the prostate do not express FSHR (FIG. 7). The absence of staining in nerves and blood vessels was also noticed in a nerve ganglion in the peripheral zone (not illustrated).

7. FSHR is expressed in the blood vessels of other human cancers.

Similar immunohistochemistry experiments have been done for other human tumor types (see Table I). The controls for all tumors consisted in normally appearing tissue located further than 10 mm outside the tumors, in the tissue obtained by surgery performed for tumor removal. The majority of the analyzed tumors (approx. 70%) were of grades I and II, approx. 25% of grade III and the remaining were the most advanced—grade IV. Representative images for each type of tumor and corresponding normal controls are shown in FIG. 8. As in the prostate, tumor cells are also occasionally and faintly stained in breast tumors and exocrine pancreatic tumors (not shown). The inventors further observed FSHR expression in blood vessels associated with a brain tumor (not shown).

A general characteristic of the vessels whose endothelial cell express FSHR is that they are located at the periphery of the tumors, in shells that have a thickness of approximately 10 mm (range 7-15 mm) and extend some few millimeters both inside and outside of the tumor, in the apparently normal tissue. No FSHR-expressing vessels are found in the more profound areas of the tumors. FIG. 9 presents quantitatively the distribution of the FSHR-expressing vessels for prostate tumors. Besides the bell-shaped distribution of the FSHR-positive vessels, the data indicate that the density of the total number of vessels (expressing or not FSHR) is higher in the interior of the tumor than in the exterior (37+/−2 (standard error) vs. 25+/−1 vessels/mm2 ($p=6\times10^{-7}$, t-test, two-tails)).

The same shell-type distribution of the FSHR-expressing EC occurs in all the tumor types examined, with the exception of approximately one third of the renal clear cell tumors, where not only the vessels at the periphery, but also in the interior of the tumors express uniformly FSHR. The percentage of the FSHR-expressing vessels reaches a maximum of 40-100% at the demarcation line between the tumor and the normal tissue, and decreases gradually to zero both towards the interior and the exterior of the tumor. The lower range, both as shell thickness and as maximum percentage of FSHR-positive vessels, occurs for exocrine pancreas and liver hepatocarcinomas, intermediate values are found for urinary bladder, ovary, lung, and stomach, and the higher range occurs for prostate, kidney, colon, breast and testis. The thickness of the shell does not appear to depend significantly on the size of the tumor.

8. FSHR is expressed in circulating blood cells. Polymorphonuclear cells isolated from prostate cancer patients express FSHR (FIG. 10 C). Mononuclear cells that are also visible in the preparation do not show any FSHR signal. FSHR positive intravascular cells are also visible in sections from prostate tumors (FIGS. 10 A and B) and tumors from colon, kidney, urinary bladder, pancreas, breast, ovary, testis, lung, stomach and liver. Higher magnification confocal microscopy reveals that the protein that generates the signal is localized at the plasma membrane, as expected for FSHR, which is a transmembrane receptor (FIG. 10 C, inset).

Quantitative data for the whole set of patients and controls, shown in FIG. 11, confirms that the cells of the healthy controls and the BPH patients do not express FSHR. The important observation for future clinical applications is that the percentage of stained cells in cancer patients is clearly proportional with the severity of the diseases, increasing rapidly from approx 15% for Gleason score 6 to over 80% for Gleason score 8.

The significance is that a test based on FSHR could easily assess the severity of the disease, and could be used to monitor the progress of the disease and the efficacy of treatments.

Discussion

Regarding the reason for FSHR expression in the tumor blood vessels, the following hypothesis can be advanced. It is conceivable that during early development, when prostate grows at a very high rate, large amounts of FSH are needed to sustain growth. Circulating FSH does not cross easily by itself the endothelial barrier [Vu Hai et al., 2004], and large amounts of FSHR on the endothelial surface may be needed to facilitate a high transport rate via transcytosis. This receptor-mediated FSH transport is probably down-regulated when the prostate reaches the mature size, but may be reactivated when the epithelium re-enters a high proliferative status in the tumors.

Regarding the mechanism that leads to the expression of FSHR in the tumor tissue, a possible inducing factor is NGF. It was reported that exogenous NGF activates FSHR expression in human ovaries [Salas et al., 2006]. NGF is expressed in prostate tumor epithelial cells [Pflug et al., 1995] and therefore FSHR expression in tumors may be induced by NGF produced by these cells.

NGF is also produced by Schwann cells [for review, Sofroniew et al., 2001], which may explain the expression of FSHR in nerves and vasa nervorum. In vitro, NGF expression by Schwann cells is upregulated by cytokines and other inflammatory mediators [Lindholm et al., 1987], which may explain the stronger staining in areas containing both nerves and inflammatory infiltrates.

Biologically active NGF is also produced and released by vascular endothelial cells, which express high and low affinity NGF receptors, TrkA and p75NGFR, respectively [Tanaka et al., 2004]. Interleukin-1, one of the proinflammatory cytokines, stimulates NGF release from endothelial cells in culture.

Exogenously added NGF to endothelial cells in culture rapidly induced tyrosine phosphorylation of TrkA, indicating that TrkA expressed on endothelial cells is capable of responding to NGF and transducing NGF signals. Possible autocrine and/or paracrine effects of NGF to vascular endothelial cells have been also predicted [Tanaka et al.2004].

A previous quantitative study reached the conclusion that no significant neoangiogenesis occurs in prostate tumors [Rubin et al., 1999]. Therefore the widespread FSHR staining cannot be restricted to the few or nonexistent newly formed vessels, and thus FSHR expression does not appear to be triggered or associated with the angiogenesis process.

Our study effectively demonstrates that FSH receptors are expressed in vessels within malignant prostate tumors. To our knowledge, this is the first demonstration of FSH receptors in vessels of any malignant tumor. The fact that FSHR is expressed in the vessels within the prostate tumors, yet is absent from the normal endothelium may have important therapeutic implications. As an integral plasma membrane protein associated with prostate cancer, FSHR offers an excellent potential selective target for monoclonal antibody-based immunotherapy and imaging.

The fact that expression of FSHR by the blood vessel endothelium was detected in all tumor types analyzed so far suggests that endothelial FSHR constitutes a general tumor marker, independent of the origin of the transformed cells.

From the perspective of using FSHR expression for in vivo tumor imaging, it should be noted that the FSHR-expressing shell represents a substantial volume compared to the total tumor volume. For instance for a tumor with a diameter of 30 mm and a volume of approx 14 cm$^3$, a shell similar to that in FIG. 9, extending from approx 3 mm inside the tumor to 7 mm outside the tumor, has a volume of approx 37 cm$^3$, 2.6 fold bigger than the tumor itself. The FSHR-positive part of the shell outside the tumor more than compensates for the lack of FSHR expression in the central part of the tumor. The ratio between the shell and the tumor volumes decreases for larger tumors, but detection of small tumors is of most interest for in vivo tumor imaging.

The presence of FSHR on the surface of the tumor endothelial cells in a wide range of tumors makes it a very promising target for both tumor imaging and therapy. FSHR could be useful for sending to the tumors agents that would destroy the tumor blood vessels or block the blood flow by inducing coagulation. The targeting agents could be either humanized anti FSHR antibodies, or FSH, or artificial ligands like aptamers. An interesting possibility, which would distinguish FSHR from other markers of the tumor vasculature, is that FSHR may mediate transcytosis of ligands across the tumor endothelium. As mentioned, transcytosis of FSHR was found to occur across the normal testis endothelium (Vu Hai et al., 2004). Repeated rounds of transcytosis may lead to accumulation of the targeted agents in the tumor, which could strongly increase both the imaging sensitivity and therapeutic efficacy. Moreover, transcytosis would allow selective delivery of agents that would destroy the tumor cells, not only the tumor ECs.

The presence of FSHR in circulating polymorphonuclear cells associated with several types of tumors further makes it possible to diagnose tumors by a simple blood test. The presented data establish the feasibility of using FSHR to detect the presence of prostate cancer starting at least with Gleason score 6, and possibly lower. (The Gleason score 6 is the lowest for which surgery is recommended.) Moreover, the test will allow monitoring of the progress of the disease and will help making decisions about the selection and efficacy of therapeutic strategies.

REFERENCES

Ablin R J, Bronson P, Soanes W A, Witebsky E. 1970a. Tissue- and species-specific antigens of normal human prostatic tissue. J Immunol 104: 1329-1339.

Ablin R J, Soanes W A, Bronson P, Witebsky E. Precipitating antigens of the normal human prostate. 1970b. J Reprod Fertil 22: 573-574.

Akin O, Hricak H. 2007. Imaging of prostate cancer. Radiol Clin N Am 45: 207-222. AIRT Working Group. 2006. Italian cancer figures-report 2006: 1. Incidence, mortality and estimates. Epidemiol Prev 30 (1 Suppl 2): 8-10.

Arap W, Haedicke W, Bernasconi M, Kain R, Rajotte D, Krajewski S, Ellerby H M, Bredesen D E, Pasqualini R, Ruoslahti E. 2002. Targeting the prostate for destruction through a vascular address. Proc Natl Acad Sci USA 99: 1527-1531.

Ben-Josef E, Yang S Y, Ji T H, Bidart J M, Garde S V, Chopra D P, Porter A T, Tang D G. 1999. Hormone-refractory prostate cancer cells express functional follicle stimulating hormone receptor (FSHR). J Urol 161: 970-976.

Bradford T J, Tomlins S A, Wang X, Chinnaiyan A M. 2006. Molecular markers of prostate cancer. Urologic Oncology 24: 538-551.

Chang S S, Reuter V E, Heston W D W, Bander N H, Grauer L S, Gaudin P B. 1999. Five different anti-prostate-specific membrane antigen (PSMA) antibodies confirm PSMA expression in tumor-associated neovasculature. Cancer Res 59: 3192-3198.

Colas P, Cohen B, Jessen T, Grishina I, McCoy J, Brent R. 1996. Genetic selection of peptide aptamers that recognize and inhibit cyclin-dependent kinase 2. Nature, 380: 548-550.

Cote R J, Morrissey D M, Houghton A N, Beattie E J Jr, Oettgen H F, Old L J. 1983. Generation of human monoclonal antibodies reactive with cellular antigens. Proc Natl Acad Sci USA. 80: 2026-2030.

De Marzo A M, Platz E A, Sutcliffe S, Xu J, Gronberg H, Drake C G, Nakai Y, Isaacs W B, Nelson W G. 2007. Inflammation in prostate carcinogenesis. Nat Rev Cancer 7: 256-269.

Eggleton P, Gargan R, Fisher D. 1989. Rapid method for the isolation of neutrophils in high yield without the use of dextran or density gradient polymers. J Immunol Methods 121: 105-113.

Hood J D, Bednarski M, Frausto R, Guccione S, Reisfeld R A, Xiang R, Cheresh D A. 2002. Tumor regression by targeted gene delivery to the neovasculature. Science 296: 2404-2407.

Jayasena S D. 1999. Aptamers: an emerging class of molecules that rival antibodies in diagnostics. Clin Chem 45: 1628-1650.

Jemal A, Siegel R, Ward E, Hao Y, Xu J, Murray T, Thun M J. 2008. Cancer statistics, 2008. CA Cancer J Clin 56: 71-96

Ji Q, Liu P I, Chen P K, Aoyama C. 2004. Follicle stimulating hormone-induced growth promotion and gene expression profiles on ovarian surface epithelial cells. Int J Cancer 112: 803-814.

Köhler G, Milstein C. Continuous cultures of fused cells secreting antibody of predefined specificity. 1975. J. Immunol. 174: 2453-2455.

Kononen J, Bubendorf L, Kallioniemi A, Barlund M, Schraml P, Leighton S, Torhorst J, Mihatsch M J, Sauter G, Kallioniemi O P. 1998. Tissue microarrays for highthroughput molecular profiling of tumor specimens. Nat Med 4: 844-847.

Leuschner C, Hansel W. 2005. Targeting breast and prostate cancers through their hormone receptors. Biol Reprod 73: 860-865.

Lindholm D, Heumann R, Meyer M, Thoenen H. 1987. Interleukin-1 regulates synthesis of nerve growth factor in non-neuronal cells of rat sciatic nerve. Nature 330: 658-659.

Macchia R J. 2004. Biopsy of the prostate-an ongoing evolution. J Urol 171: 1487-1488.

Macklon N S, Fauser BCJM. 1998. Follicle development during the normal menstrual cycle. Maturitas 30: 181-188.

Maecke H R, Hofmann M, Haberkorn U. 2005. 68Ga-labeled peptides in tumor imaging. J Nucl Med 46 (Suppl 1): 172S-178S.

Mariani S, Salvatori L, Basciani S, Arizzi M, Franco G, Petrangeli E, Spera G, Gnessi L. 2006. Expression and cellular localization of follicle-stimulating hormone receptor in normal human prostate, benign prostatic hyperplasia and prostate cancer. J Urol 175: 2072-2077.

Minegish, T.; Nakamura, K.; Takakura, Y.; Ibuki, Y.; Igarashi, M. 1991. Cloning and sequencing of human FSH receptor cDNA. Biochem. Biophys. Res. Commun. 175: 1125-1130.

Parry R, Schneider D, Hudson D, Parkes D, Xuan J A, Newton A, Toy P, Lin R, Harkins R, Alicke B, Biroc S, Kretschmer P J, Halks-Miller M, Klocker H, Zhu Y, Larsen B, Cobb R R, Bringmann P, Roth G, Lewis J S, Dinter H, Parry G. 2005. Identification of a novel prostate tumor target, mindin/RG-1, for antibody-based radiotherapy of prostate cancer. Cancer Res. 65: 8397-8405

Pflug B R, Dionne C, Kaplan D R, Lynch J, Djakiew D. 1995. Expression of a Trk high affinity nerve growth factor receptor in the human prostate. Endocrinology 136: 262-268.

Plant T M, Marshall G R. 2001. The functional significance of FSH in spermatogenesis and the control of its secretion in male primates. Endocr Rev 22: 764-786.

Powell M S, Li R, Dai H, Sayeeduddin M, Wheeler T M, Ayala G E. 2005. Neuroanatomy of the normal prostate. Prostate 65: 52-57.

Remzi M, Fong Y K, Dobrovits M, Anagnostou T, Seitz C, Waldert M, Harik M, Marihart S, Marberger M, Djavan B. 2005. The Vienna nomogram: validation of a novel biopsy strategy defining the optimal number of cores based on patient age and total prostate volume. J Urol 174: 1256-1260.

Rubin M A, Buyyounouski M, Bagiella E, Sharir S, Neugut A, Benson M, de la Taille A, Katz A E, Olsson C A, Ennis R D. 1999. Microvessel density in prostate cancer: lack of correlation with tumor grade, pathologic stage, and clinical outcome. Urology 53: 542-547.

Salas C, Julio-Pieper M, Valladares M, Pommer R, Vega M, Mastronardi C, Kerr B, Ojeda S R, Lara H E, Romero C. 2006. Nerve growth factor-dependent activation of trkA receptors in the human ovary results in synthesis of follicle-stimulating hormone receptors and estrogen secretion. J Clin Endocrinol Metab 91: 2396-2403.

Simoni M, Gromoll J, Nieschlag E. 1997. The follicle stimulating hormone receptor. Biochemistry, molecular biology, physiology and pathophysiology. Endocr Rev 18: 739-773, Simionescu N, Simionescu M. 1988. The cardiovascular system. In: Cell and Tissue Biology. A textbook of histology. Weiss L (ed) Sixth edition, Urban & Schwarzenberg, Baltimore, Munich, pp 355-400.

Scardino P T. 2003. The Prevention of Prostate Cancer. The Dilemma Continues. N Engl J Med 349: 297-299.

Sofroniew M V, Hove C L, Mobley W C. 2001. Nerve growth factor signalling, neuroprotection, and neural repair. Annu Rev Neurosci 24: 1217-1281.

Sprengel R, Braun T, Nikolics K, Segaloff D L, Seeburg P H. 1990. The testicular receptor for follicle-stimulating hormone: structure and functional expression of cloned cDNA. Mol Endocrinol 4: 525-530.

Stamey T A, Caldwell M, McNeal J E, Nolley R, Hemenez M, Downs J. 2004. The prostate specific antigen era in the United States is over for prostate cancer: What happened in the last 20 years? J Urol 172: 1297-1301.

Stenman U H, Abrahamsson P A, Aus G, Lilja H, Bangma C, Hamdy F C, Boccon-Gibod L, and Ekman P. 2005. Prognostic value of serum markers for prostate cancer. Scand J Urol Nephrol Suppl 216: 64-81.

Tanaka A, Wakita U, Kambe N, Iwasaki T, Matsuda H. 2004. An autocrine function of nerve growth factor for cell cycle regulation of vascular endothelial cells. Biochem Biophys Res Commun 313: 1009-1104.

Tolivia J, Navarro A, del Valle E, Perez C, Ordonez C, Martinez E. 2006. Application of Photoshop and Scion Image analysis to quantification of signals in histochemistry, immunocytochemistry and hybridocytochemistry. Anal Quant Cytol Histol. 28: 43-53.

Tuerk C. 1997. Using the SELEX combinatorial chemistry process to find high affinity nucleic acid ligands to target molecules. Methods Mol Biol 67: 219-230.

Vannier B, Loosfelt H, Meduri G, Pichon C, Milgrom E. 1996. Anti-human FSH receptor monoclonal antibodies: immunochemical and immunocytochemical characterization of the receptor. Biochemistry 35: 1358-1366.

Vu Hai M T, Lescop P, Loosfelt H, Ghinea N. 2004. Receptor-mediated transcytosis of follicle stimulating hormone through the rat testicular microvasculature. Biol Cell 96: 133-144.

Wilson, S S. 2005. Prostate cancer screening. Comprehensive Therapy 31: 119-123.

Zhu L, Koistinen H, Wu P, Narvanen A, Schallmeiner E, Fredriksson S, Landegren U, Stenman U H. 2006. A sensitive proximity ligation assay for active PSA. Biol Chem 387: 769-772.

The invention claimed is:

1. A method for imaging vessels associated with a tumor in a patient, the method comprising administering a labeled Vascular Endothelial follicle-stimulating hormone (FSH) receptor (VE-FSHR) ligand to said patient and imaging said patient to detect the in vivo binding of said ligand to a VE-FSHR in vessels associated with the tumor in said patient.

2. The method according to claim 1, wherein the FSH receptor (FSHR) ligand is a detectably labeled anti-FSHR antibody.

3. The method according to claim 1, wherein the FSH receptor (FSHR) ligand is detectably labeled FSH.

4. The method according to claim 1, wherein said tumor is selected from the group consisting of prostate, kidney, ovary, testis, lung, liver, pancreas, stomach, breast, colon, brain and urinary bladder cancer.

5. The method according to claim 4, wherein the prostate cancer is prostate adenocarcinoma.

6. The method according to claim 1, wherein the FSH receptor (FSHR) ligand localizes or determines the size of the tumor in vivo.

7. The method according to claim 1, wherein said method evaluates the severity of a cancer or monitors the efficacy of an anti-tumor therapy.

8. The method according to claim 1, wherein the FSH receptor (FSHR) ligand is administered intravenously.

9. The method according to claim 1, wherein said FSH receptor (FHSR) ligand is labeled with a gas-filled microvesicle.

10. The method according to claim 1, wherein said method comprises contrast enhanced ultrasound imaging.

11. The method according to claim 1, wherein the tumor is a primary tumor or a metastatic lesion.

12. The method according to claim 1, wherein said vessels are blood vessels associated with the tumor.

13. The method according to claim 1, wherein said vessels are microvessels associated with the tumor.

* * * * *